US00PP30870P2

(12) United States Plant Patent
Klemm et al.

(10) Patent No.: US PP30,870 P2
(45) Date of Patent: Sep. 3, 2019

(54) ***DIANTHUS* PLANT NAMED 'KLEDG18267'**

(50) Latin Name: ***Dianthus* sp.**
Varietal Denomination: KLEDG18267

(71) Applicant: Klemm+Sohn GmbH & Co. KG, Stuttgart (DE)

(72) Inventors: Nils Klemm, Stuttgart (DE); Lena Gutbrodt, Bempflingen (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 15/998,299

(22) Filed: Aug. 1, 2018

(51) Int. Cl.
*A01H 5/02* (2018.01)
*A01H 6/30* (2018.01)

(52) U.S. Cl.
USPC ..... Plt./277

(58) Field of Classification Search
USPC ..... Plt./272, 273, 277
See application file for complete search history.

*Primary Examiner* — Susan McCormick Ewoldt
(74) *Attorney, Agent, or Firm* — Barbara Campbell; Cochran Freund & Young LLC

(57) ABSTRACT

A new *Dianthus* plant designated 'KLEDG18267' particularly distinguished by dark pink double flowers with red-purple eyes and an upright habit, is disclosed.

1 Drawing Sheet

Genus and species: *Dianthus* sp.
Variety denomination: 'KLEDG18267'.

CROSS-REFERENCE TO RELATED APPLICATIONS

A Canada Plant Breeders Rights application was filed for this variety on Apr. 27, 2018, Application No. 18-9430 and a European Community Plant Variety Rights application was filed on Apr. 24, 2018, File No. 2018/1127. 'KLEDG18267' has not been made publicly available or sold more than one year prior to the filing date of the present application.

BACKGROUND OF THE NEW PLANT 'KLEDG18267'

The present invention comprises a new and distinct variety of *Dianthus*, botanically known as *Dianthus* sp., and hereinafter referred to by the variety name 'KLEDG18267'. 'KLEDG18267' originated from a hand pollination of two proprietary *Dianthus* varieties in June 2003 in Stuttgart, Germany. The female parent was the proprietary *Dianthus* variety 'DCP-2008-0137' (unpatented) and the male parent was the proprietary *Dianthus* variety 'DSS-2011-0099' (unpatented). 'KLEDG18267' was selected in the June 2014.

In September 2014, 'KLEDG18267' was first vegetatively propagated by vegetative stem cuttings in Stuttgart, Germany and was subsequently propagated in Latina, Italy. 'KLEDG18267' was found to reproduce true to type in successive generations of asexual propagation in Stuttgart, Germany and Latina, Italy via vegetative stem cuttings.

SUMMARY OF 'KLEDG18267'

The following are the most outstanding and distinguishing characteristics of 'KLEDG18267' when grown under normal horticultural practices in Stuttgart, Germany.

1. Dark pink double flowers with red-purple eyes; and
2. An upright habit.

DESCRIPTION OF THE PHOTOGRAPH

This new *Dianthus* plant is illustrated by the accompanying photograph of a plant approximately 10-months old and grown in a greenhouse in Stuttgart, Germany. The photograph shows the whole plant, including the flowers and foliage and buds and were taken in September 2015 in Stuttgart, Germany. The colors shown are as true as can be reasonably obtained by conventional photographic procedures.

DESCRIPTION OF 'KLEDG18267'

The following detailed descriptions set forth the distinctive characteristics of 'KLEDG18267'. The data which define these characteristics were collected from asexual reproductions carried out in Stuttgart, Germany. Data was collected in April 2018 on 8-month old plants grown in a greenhouse. Color references are to The R.H.S. Colour Chart of The Royal Horticultural Society of London (R.H.S.), 5$^{th}$ edition (2007).

Classification:
- *Family*.—Caryophyllaceae.
- *Botanical*.—*Dianthus* sp.
- *Common*.—Pot carnation.
- *Designation*.—'KLEDG18267'.

Parentage:
- *Female parent*.—The proprietary *Dianthus* variety 'DCP-2008-0137' (unpatented).
- *Male parent*.—The proprietary *Dianthus* variety 'DSS-2011-0099' (unpatented).

Plant:
- *Plant form*.—Upright.
- *Plant height*.—6.0 cm to 8.0 cm.
- *Plant diameter or spread*.—18.0 cm to 20.0 cm.
- *Propagation type*.—Vegetative stem cuttings.

*Time to produce a rooted young plant.*—10 to 14 days.
*Rooting habit (shape).*—Lanceolate.

Lateral branches:
*Length.*—6.0 cm to 8.0 cm.
*Diameter.*—2.0 cm to 3.0 cm.
*Internode length.*—0.2 cm to 0.3 cm.
*Number of internodes per branch/stem.*—4 to 6.
*Node length.*—0.15 cm.
*Node diameter.*—0.15 cm.
*Texture.*—Smooth.
*Color.*—RHS N138A.
*Branch/stem appearance.*—Solid.

Foliage:
*Type.*—Sessile.
*Arrangement.*—Opposite.
*Length.*—2.0 cm to 3.0 cm.
*Width.*—0.2 cm to 0.4 cm.
*Shape.*—Lanceolate.
*Apex.*—Acute.
*Base.*—Obtuse.
*Margin.*—Entire.
*Texture (both upper and lower surfaces).*—Smooth.
*Immature leaf color.*—Upper surface: RHS 138A. Lower surface: RHS N138B.
*Mature leaf color.*—Upper surface: RHS 139A. Lower surface: RHS N138B.
*Venation color.*—Upper surface: RHS 139A. Lower surface: RHS N138B.

Flowers:
*Flower type and habit.*—Double, round, small sprays.
*Fragrance.*—Present.
*Natural flowering season.*—Spring to fall.
*Position of flowers relative to the foliage.*—Slightly above.
*Diameter of the flower.*—3.0 cm to 4.0 cm.
*Number of flowers per spray.*—2 to 4.
*Diameter of the spray.*—7.0 cm to 9.0 cm.
*Flower longevity on the plant.*—14 to 21 days.
*Buds.*—Length: 1.5 cm to 1.8 cm. Diameter: 0.6 cm to 0.8 cm. Shape: Elliptic. Color: RHS 147A, RHS 144B, and RHS 183A. Extrusion of the styles at the bud stage: Absent.
*Corolla.*—Quantity of petals and arrangement: 15 to 20 in spiral whorls. Corolla height: 1.5 cm. Petal length: 3.5 cm. Petal width: 1.5 cm to 2.0 cm. Petal shape: Spoon-shaped. Petal apex: Obtuse. Petal base: Acute. Petal margin: Crenate. Depth of petal margin: Medium. Petal texture (both upper and lower surfaces): Smooth. Petal color: Immature: Upper surface: RHS 61B with RHS 187B eyes. Lower surface: RHS 64B. Mature: Upper surface: RHS 71C with RHS 59A eyes. Lower surface: RHS N74B.
*Calyx.*—Quantity of sepals and arrangement: Composed of 5 sepals, fused. Shape: Campanulate. Calyx height: 1.8 cm to 2.0 cm. Calyx diameter (at the apex): 0.8 cm to 1.0 cm. Sepal texture (both upper and lower surfaces): Smooth. Sepal color: Upper surface: RHS 146A, RHS 183B, and RHS 144B. Lower surface: RHS 146C.

Peduncles:
*Length.*—6.0 cm to 8.0 cm.
*Diameter.*—0.2 cm.
*Strength.*—Moderate.
*Texture.*—Smooth.
*Color.*—RHS 137A.

Reproductive organs:
*Stamens.*—Quantity per flower: 3 to 5. Filament length: 0.5 cm to 0.7 cm. Filament color: RHS NN155A. Anther length: 0.1 cm. Anther diameter: 0.05 cm. Anther color: RHS 75A. Pollen amount: Sparse.
*Pistils.*—Quantity per flower: 1. Pistil length: 1.4 cm to 1.8 cm. Style length: 0.8 cm to 1.0 cm. Style color: RHS N155A. Stigma shape: Filamentous. Stigma color: RHS 75A. Ovary size: 0.6 cm to 0.8 cm. Ovary shape: Oval. Ovary color: RHS 150B.

Fruit and seed set: Seed is sometimes observed, but no information on the seed is available.

Disease and pest/insect resistance: No disease and pest/insect resistance observed.

COMPARISON OF 'KLEDG18267' WITH PARENTAL LINE AND KNOWN VARIETY

'KLEDG18267' is distinguished from the mutation parent as described in Table 1.

TABLE 1

Comparison with Parental Line

| Characteristic | 'KLEDG18267' | Female parent 'DCP-2008-0137' | Male parent 'DSS-2011-0099' |
|---|---|---|---|
| Flower longevity on the plant | 2 to 4 weeks | 1 to 2 weeks | 1 to 2 weeks |
| Flower size | Large, filled flowers | Smaller flowers, semi double | Smaller flowers, semi double |

'KLEDG18267' can be compared to the commercial *Dianthus* variety 'KLEDP14206' (U.S. Plant Pat. No. 26,846), also known as OSCAR 'Purple Wings'. Differences between the varieties are described in Table 2.

TABLE 2

Comparison with Similar Variety

| Characteristic | 'KLEDG18267' | 'KLEDP14206' |
|---|---|---|
| Flower longevity on the plant | 2 to 4 weeks | 1 to 2 weeks |
| Winter hardiness | Winter hardy | Not winter hardy |

We claim:

1. A new and distinct variety of *Dianthus* plant designated 'KLEDG18267' as illustrated and described herein.

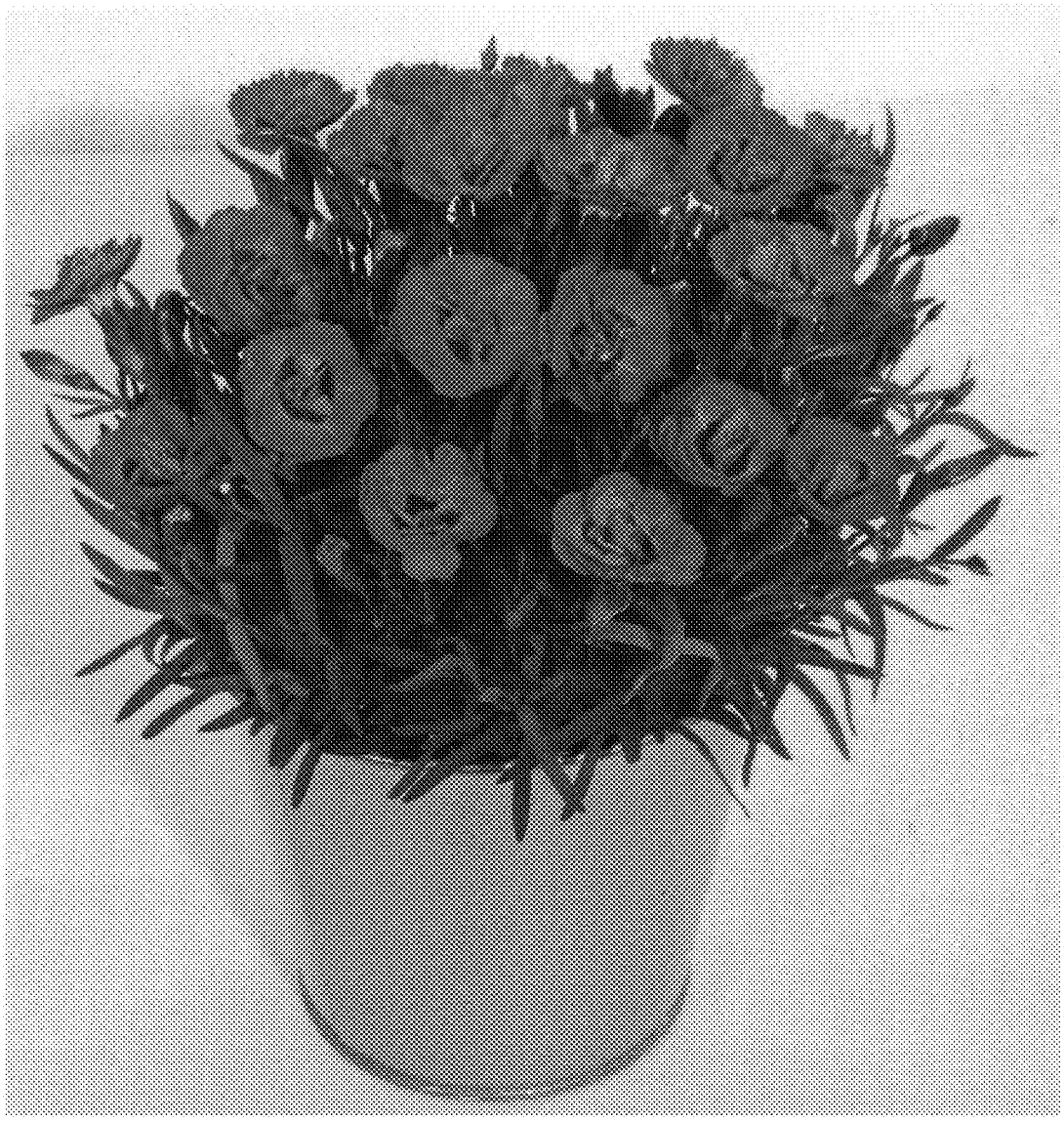

* * * * *